(12) United States Patent
Staton

(10) Patent No.: US 10,392,167 B2
(45) Date of Patent: Aug. 27, 2019

(54) VENTABLE CLOSURE WITH PORT

(75) Inventor: John M. Staton, Fairport, NY (US)

(73) Assignee: Nalge Nunc International Corporation, Rochester, NY (US)

( * ) Notice: Subject to any disclaimer, the term of this patent is extended or adjusted under 35 U.S.C. 154(b) by 1294 days.

(21) Appl. No.: 14/366,173

(22) PCT Filed: Oct. 12, 2011

(86) PCT No.: PCT/US2011/055975
§ 371 (c)(1),
(2), (4) Date: Mar. 26, 2015

(87) PCT Pub. No.: WO2012/051307
PCT Pub. Date: Apr. 19, 2012

(65) Prior Publication Data
US 2015/0203258 A1    Jul. 23, 2015

Related U.S. Application Data

(60) Provisional application No. 61/404,965, filed on Oct. 12, 2010.

(51) Int. Cl.
*B65D 47/00* (2006.01)
*B65D 47/32* (2006.01)
(Continued)

(52) U.S. Cl.
CPC .............. *B65D 47/32* (2013.01); *B01L 3/567* (2013.01); *B67B 6/00* (2013.01); *B67C 3/02* (2013.01);
(Continued)

(58) Field of Classification Search
CPC . B65D 47/32; B01L 3/567; B01L 2200/0684; B01L 2300/048;
(Continued)

(56) References Cited

U.S. PATENT DOCUMENTS 3,158,553 A    11/1964 Carski
3,326,401 A *   6/1967 De Long .............. B65D 51/002
                                                        215/261
(Continued)

FOREIGN PATENT DOCUMENTS

EP    0500249 A1    8/1992
EP    1621474 A1    2/2006
(Continued)

OTHER PUBLICATIONS

ISA/US, International Search Report and Written Opinion of the International Searching Authority, International Application No. PCT/US2011/055975, dated Mar. 20, 2012 (11 pages).
(Continued)

*Primary Examiner* — Ernesto A Grano

(57) ABSTRACT

A closure (10, 100, 150) for a labware device (20). The labware device (20) defines an interior chamber (25) having at least one opening (92). The closure (10, 100, 150) includes a closure body (12, 102) configured to be mounted to the labware device (20) and in fluid communication with the opening (92). A vent valve (14, 122) is mounted for movement relative to the closure body (12, 102). The vent valve (14, 122), with the closure body (12, 102), defines a space (72, 120) that defines a path between the closure body (12, 102) and the vent valve (14, 122) for gas exchange between the interior chamber (25) and the exterior of the labware device (20). A filter (50) is positioned within the space (72, 120) and is configured to filter contaminants from gas entering the interior chamber (25) via the path.

7 Claims, 12 Drawing Sheets

(51) Int. Cl.
  *B01L 3/00* (2006.01)
  *C12M 1/12* (2006.01)
  *C12M 1/00* (2006.01)
  *B67B 6/00* (2009.01)
  *B67C 3/02* (2006.01)

(52) U.S. Cl.
  CPC ............ *C12M 23/04* (2013.01); *C12M 23/38* (2013.01); *B01L 2200/0684* (2013.01); *B01L 2300/048* (2013.01); *B01L 2300/049* (2013.01); *B01L 2300/10* (2013.01)

(58) Field of Classification Search
  CPC .. B01L 2300/049; B01L 2300/10; B67C 6/00; B67C 3/02; C12M 23/04; C12M 23/38
  USPC ....................................................... 220/371
  See application file for complete search history.

(56) References Cited

U.S. PATENT DOCUMENTS

| | | | |
|---|---|---|---|
| 4,036,386 A | 7/1977 | Nishioka et al. | |
| 4,327,842 A * | 5/1982 | Walter | B65D 47/141 215/237 |
| 4,437,574 A * | 3/1984 | Ruklic | B65D 47/0842 215/247 |
| 5,047,347 A * | 9/1991 | Cline | C12M 23/08 220/371 |
| 5,240,854 A | 8/1993 | Berry et al. | |
| 5,353,949 A | 10/1994 | Seibert et al. | |
| 5,391,496 A * | 2/1995 | Kayal | C12M 23/08 215/308 |
| 5,395,006 A * | 3/1995 | Verma | B65D 51/1611 215/261 |
| 5,398,837 A | 3/1995 | Degrassi | |
| 5,523,236 A | 6/1996 | Nuzzo | |
| 5,732,837 A | 3/1998 | Jones | |
| 5,752,746 A | 5/1998 | Perry | |
| 5,958,778 A * | 9/1999 | Kidd | B01L 3/5021 422/548 |
| 5,988,449 A | 11/1999 | Fuchs et al. | |
| 6,095,356 A * | 8/2000 | Rits | B65D 51/1616 215/261 |
| 6,312,648 B1 * | 11/2001 | Lenardo | B01L 3/50825 422/501 |
| 6,375,028 B1 * | 4/2002 | Smith | B01L 3/50825 215/278 |
| 6,569,675 B2 | 5/2003 | Wall et al. | |
| 6,619,499 B1 | 9/2003 | Lin | |
| 7,745,209 B2 * | 6/2010 | Martin | C12M 23/04 435/294.1 |
| 7,745,210 B2 * | 6/2010 | Martin | C12M 23/08 215/40 |
| 7,857,515 B2 * | 12/2010 | Dais | B65D 33/25 24/585.12 |
| 7,867,761 B2 | 1/2011 | Esser et al. | |
| 7,886,412 B2 * | 2/2011 | Dais | B65D 81/2023 24/399 |
| 7,897,379 B2 * | 3/2011 | Kenney | B01L 3/08 435/297.5 |
| 7,954,659 B2 * | 6/2011 | Zuares | B65D 47/0804 220/254.3 |
| 9,309,491 B2 * | 4/2016 | Martin | C12M 23/24 |
| 2002/0066752 A1 | 6/2002 | Ritsche et al. | |
| 2002/0100739 A1 | 8/2002 | Day et al. | |
| 2004/0072347 A1 | 4/2004 | Schuler et al. | |
| 2006/0283896 A1 * | 12/2006 | Kasting | B65D 47/24 222/549 |
| 2007/0065933 A1 | 3/2007 | Esser et al. | |
| 2007/0187409 A1 | 8/2007 | Wilford et al. | |
| 2010/0084397 A1 | 4/2010 | Kubo et al. | |
| 2010/0136686 A1 | 6/2010 | Wilson | |

FOREIGN PATENT DOCUMENTS

| | | |
|---|---|---|
| JP | 06-201894 A | 7/1994 |
| JP | 8173146 A | 7/1996 |
| JP | 11506933 A | 6/1999 |
| JP | 2002323143 A | 11/2002 |
| JP | 2002355027 A | 12/2002 |
| JP | 200934078 A | 2/2009 |
| JP | 2010518879 A | 6/2010 |
| WO | 9639533 A1 | 12/1996 |
| WO | 0222458 A1 | 3/2002 |
| WO | 2010/008566 A3 | 1/2010 |

OTHER PUBLICATIONS

The International Bureau of WIPO, International Preliminary Report on Patentability, International Application No. PCT/US2011/055975, dated Apr. 25, 2013 (9 pages).
Corning Incorporated, CellCube Culture System, User's Manual, Rev. V1.02, Corning Cat. No. 3143, 2011 (68 pages).
Corning Incorporated, Corning CellSTACK Culture Chambers, Instructions for Use, POD CLS-BP-007 REV5, 2007 (4 pages).
Thermo Fisher Scientific Inc., Thermo Scientific Nunc Cell Factory Brochure, Instructions for use: CF1, CF4, CF10 and CF40, dated 2010 (2 pages).
Corning Incorporated, Corning CellBIND Surface CellSTACK Culture Chambers, CLS3320-10 chamber, surface treatment Corning CellBIND, retrieved from http://www.sigmaaldrich.com/catalog/ProductDetail on Aug. 9, 2011 (1 page).
Corning Incorporated, Corning CellSTACK Culture Chambers, CLS3272-40 chamber, surface treatment TC-Treated, retrieved from http://www.sigmaaldrich.com/catalog/ProductDetail, retrieved on Aug. 9, 2011 (1 page).
The Industrial Property Digital Library, Patent Abstracts of Japan, Publication No. 06-201894, published on Jul. 22, 1994, retrieved from http://www19.ipdl.inpit.go.jp/PA1/cgi-bin/PA1INDEX on Nov. 21, 2014 (1 page).
Chinese Patent Office, English Translation of the First Office Action, Application No. 201180058582.3, dated Sep. 2, 2014 (13 pages).
Chinese Patent Office, First Office Action, Application No. 201180058582.3, dated Sep. 2, 2014 (15 pages).
Australian Intellectual Property Office, Patent Examination Report No. 1, Application No. 2011316628, dated Nov. 28, 2014 (4 pages).
Mexican Patent Office, Office Action, Patent Application No. MX/a/2013/004170, dated Apr. 13, 2015 (6 pages).
Mexican Patent Office, English Translation of Office Action, Patent Application No. MX/a/2013/004170, dated Apr. 13, 2015 (6 pages).
Japanese Patent Office, Office Action, Patent Application No. 2013-533974, dated May 18, 2015 (6 pages).
Japanese Patent Office, English Translation of Office Action, Patent Application No. 2013-533974, dated May 18, 2015 (7 pages).
Japanese Patent Office, English Translation of Abstract for JP2009034078A, published on Feb. 19, 2009 (1 page).
ESPACENET, English Machine Translation of Abstract for JP2002355027A, published on Dec. 10, 2002, retrieved from http://worldwide.espacenet.com on Jun. 4, 2015 (2 pages).
ESPACENET, English Machine Translation of Abstract for JP2010518879A, published on Jun. 3, 2010, retrieved from http://worldwide.espacenet.com on Jun. 4, 2015 (2 pages).
ESPACENET, English Machine Translation of Abstract for JP2002323143A, published on Nov. 8, 2002, retrieved from http://worldwide.espacenet.com on Jun. 4, 2015 (2 pages).
Mexican Patent Office, Office Action, Mexican Patent Application No. MX/A/2013/004170, dated Jul. 12, 2016 (6 pages).
Chinese Patent Office, Second Office Action, Chinese Patent Application No. 201180058582.3, dated Jul. 1, 2015 (3 pages).
Chinese Patent Office, English Translation of Second Office Action, Chinese Patent Application No. 201180058582.3, dated Jul. 1, 2015 (1 page).
Canadian Patent Office, Office Action, Application No. 2,814,408, dated Sep. 27, 2017 (3 pages).
European Patent Office, Supplementary European Search Report, Application No. EP11833339, dated Oct. 30, 2017 (8 pages).

(56) References Cited

OTHER PUBLICATIONS

Australian Patent Office, Examination report No. 1 for standard patent application, Application No. 2016219699, dated Sep. 1, 2017 (8 pages).
Intellectual Property India, Examination Report, Application No. 3209/DELNP/2013, dated Oct. 4, 2018 (8 pages).

* cited by examiner

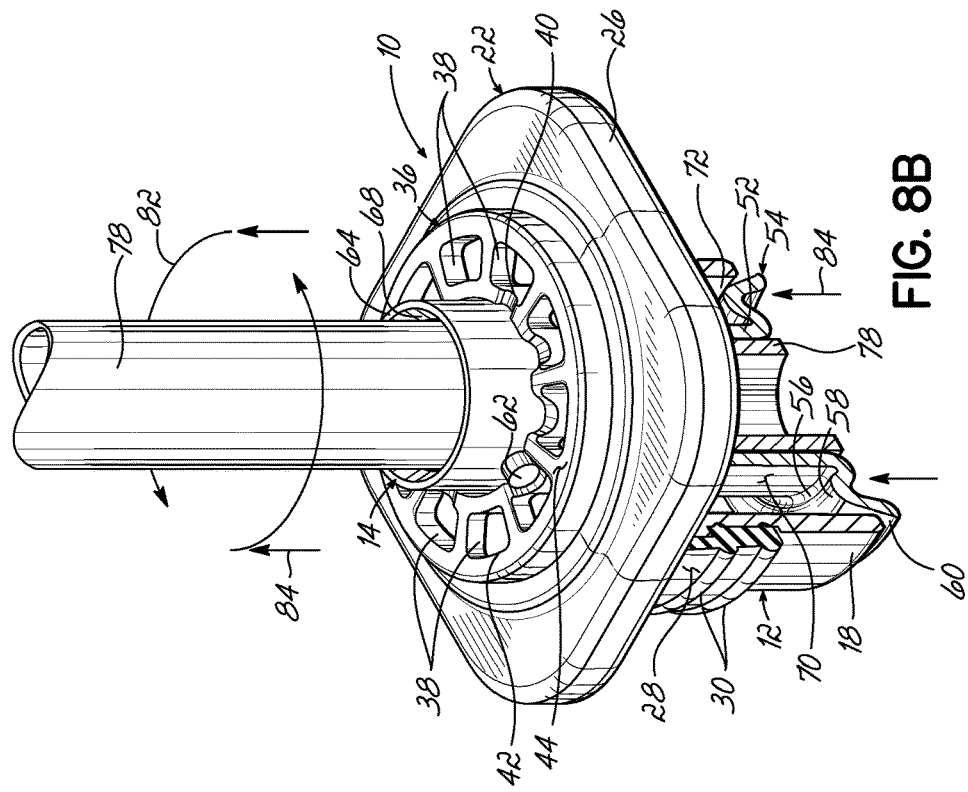
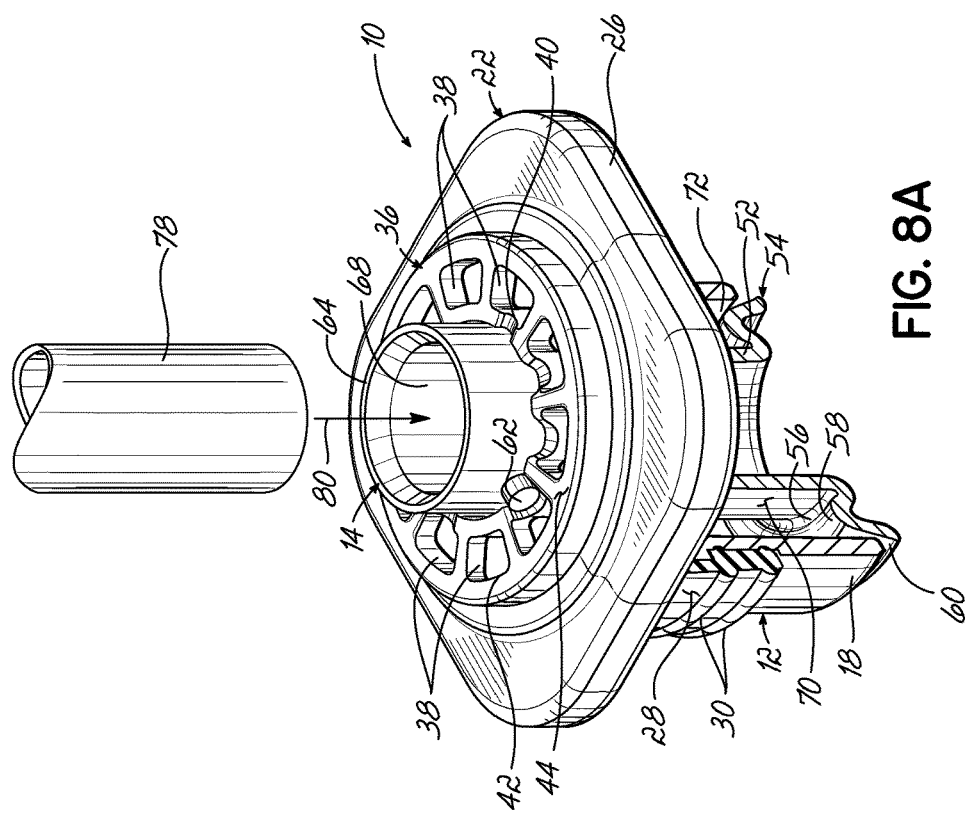

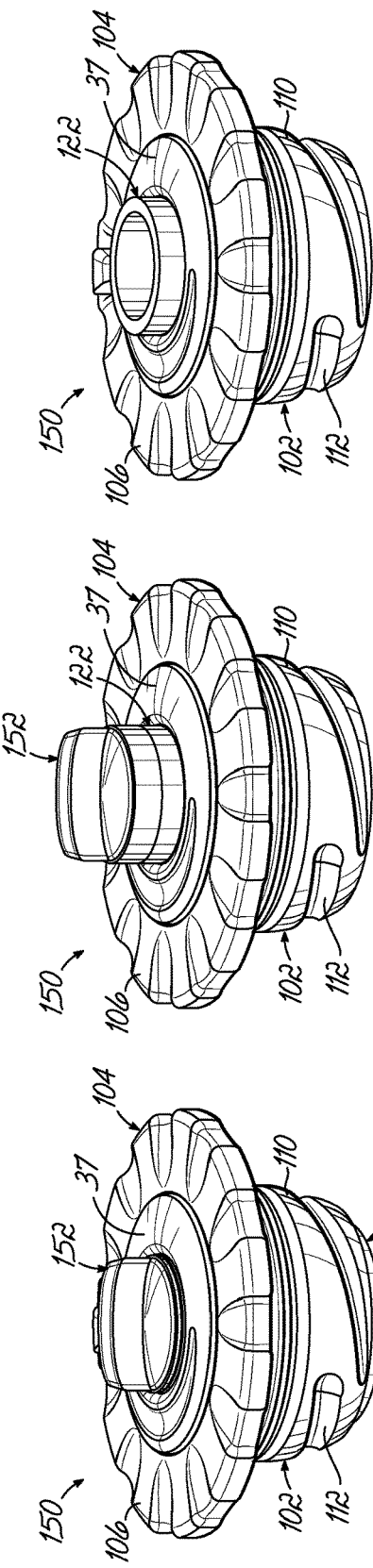

VENTABLE CLOSURE WITH PORT

The present application claims the filing benefit of U.S. Provisional Application Ser. No. 61/404,965, filed Oct. 12, 2010, the disclosure of which is hereby incorporated by reference herein in its entirety.

FIELD OF THE INVENTION

The present invention relates generally to port plugs and, more specifically, to port plugs that permit gas exchange in a cell culture device.

BACKGROUND OF THE INVENTION

Adequate gas exchange between the gaseous contents or air-space within a cell culture container and the gaseous environment within which the container is stored is generally critical to achieving cell growth and/or function. Gas exchange may occur via a variety of features including a closure within a port opening of the cell culture container. Closures may have a vent state, for example, wherein space between closure and container is created. Alternatively, the closure may contain a region comprising a gas permeable membrane, film, or filter that permits gas exchange.

However, use of the conventional closures in a vent state causes the cell culture to be susceptible to microbial contamination by passage via the airflow space. While conventional closures having an area containing a gas permeable membrane may protect against microbial contamination, gas exchange may not be limited or restricted, such as in when the culture container is moved from a growth environment to a different environment (such as ambient air in a laminar flow hood) for examination and/or manipulation of the culture.

Accordingly, it would be advantageous to have a closure that is capable of reversibly venting the cell culture container while reducing the risk of microbial contamination and maintaining the ability to open a port for fluid communication with the cell culture container.

SUMMARY OF THE INVENTION

The present invention overcomes the foregoing problems and other shortcomings, drawbacks, and challenges of conventional, ventable cell culture containers by reducing susceptibility to microbial contamination and increasing functionality of the port. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a closure for a labware device defining an interior chamber having at least one opening. The closure includes a closure body configured to be mounted to the labware device and in fluid communication with the opening. A vent valve is mounted for movement relative to the closure body. The vent valve, with the closure body, defines a space that defines a path between the closure body and the vent valve for gas exchange between the interior chamber and the exterior of the labware device. A filter is positioned within the space and is configured to filter contaminants from any gas entering the interior chamber via the path.

According to another embodiment of the present invention, a method of venting an opening of a labware device is provided. The labware device defines an interior chamber and has the opening in fluid communication with the interior chamber and, wherein the labware device includes at least one opening and a closure device positioned within the opening. The method comprises selectively and variably venting the opening so that gas exchange between the interior chamber and the exterior of the labware device is provided. The opening is sealed to resist fluid communication.

In accordance with still another embodiment of the present invention, a method of venting an opening of a labware device is provided. The labware device defines an interior chamber and has the opening in fluid communication with the interior chamber and, wherein the labware device includes at least one opening and a closure device positioned within the opening. The method comprises selectively venting the opening so that gas exchange between the interior chamber and the exterior of the labware device is provided. A port in the closure is selectively opened, wherein the port extends through the opening and provides for the addition of fluid to or the removal of fluid from the interior chamber.

According to another embodiment of the present invention, a method of venting an opening of a labware device is provided. The labware device defines an interior chamber and has the opening in fluid communication with the interior chamber and, wherein the labware device includes at least one opening and a closure device positioned within the opening. The method comprises selectively venting the opening so that gas exchange between the interior chamber and the exterior of the labware device is provided. The opening is sealed to resist fluid communication. A port in the closure is selectively opened, wherein the port extends through the opening and provides for the addition of fluid to or the removal of fluid from the interior chamber.

Yet another embodiment of the present invention is directed a closure for a labware device defining an interior chamber having at least one opening. The closure includes a closure body configured to be mounted to the labware device and in fluid communication with the opening. A vent valve is mounted for movement relative to the closure body. The vent valve, with the closure body, defines a space that defines a first path between the closure body and the vent valve for gas exchange between the interior chamber and the exterior of the labware device. A filter is positioned within the space and is configured to filter contaminants from gas entering the interior chamber via the first path. A closable port extends through the vent valve and defines a second path in fluid communication with the interior chamber.

The above and other objects and advantages of the present invention shall be made apparent from the accompanying drawings and the descriptions thereof.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIG. 8A is a perspective view of the closure, with the sealing portion shown in cross-section and in the vent state, and with the port cap removed and a tubing positioned to be inserted through the port.

FIG. 8B is a perspective view of the closure, with the sealing portion shown in cross-section and in the vent state, and with the tubing extending through the port.

FIGS. 11A-11C are a series of perspective views of a closure and a method of using the same in accordance with another embodiment of the present invention.

FIGS. 12A-12C are cross-sectional views of the closure of FIGS. 11A-11C, respectively.

DETAILED DESCRIPTION OF THE INVENTION

Figure 1:
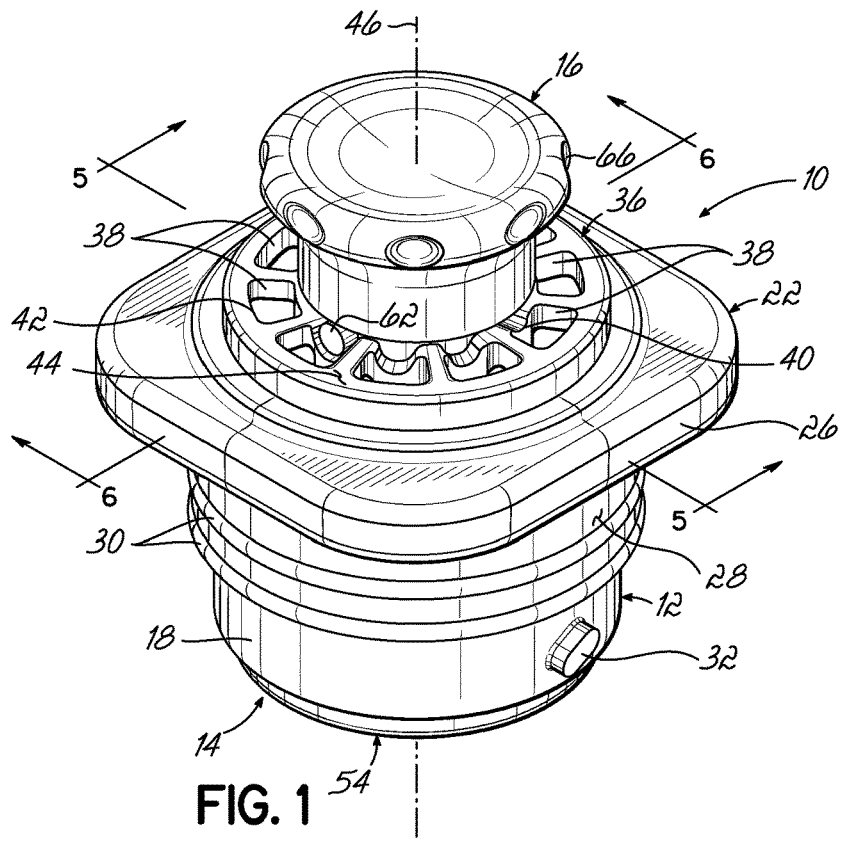
FIG. 1 is a perspective view of a closure for an opening in a labware device in accordance with one embodiment of the present invention.
Figure 2:
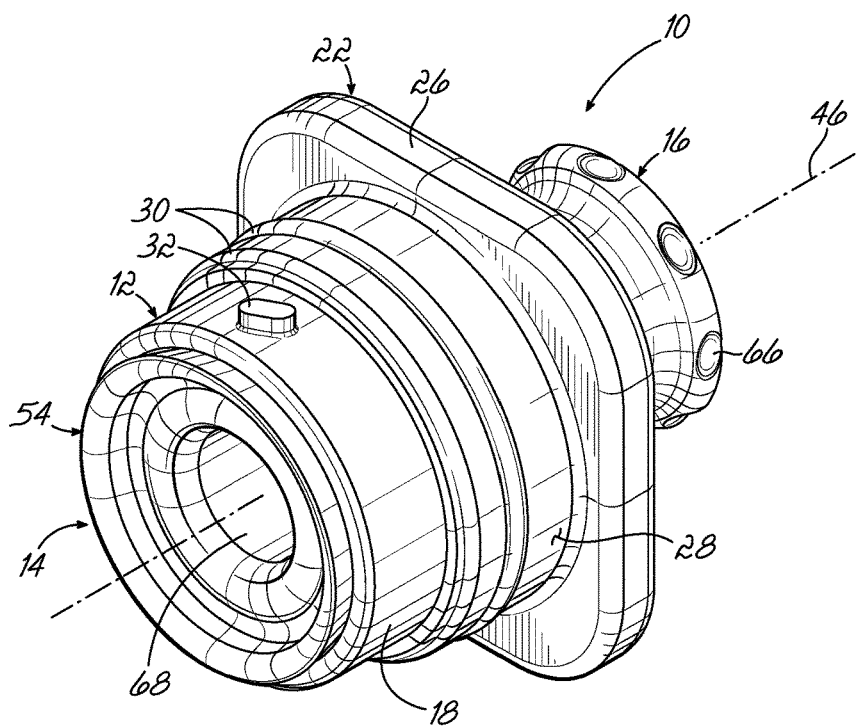
FIG. 2 is a bottom-side view of the closure shown in FIG. 1.
Figure 3:
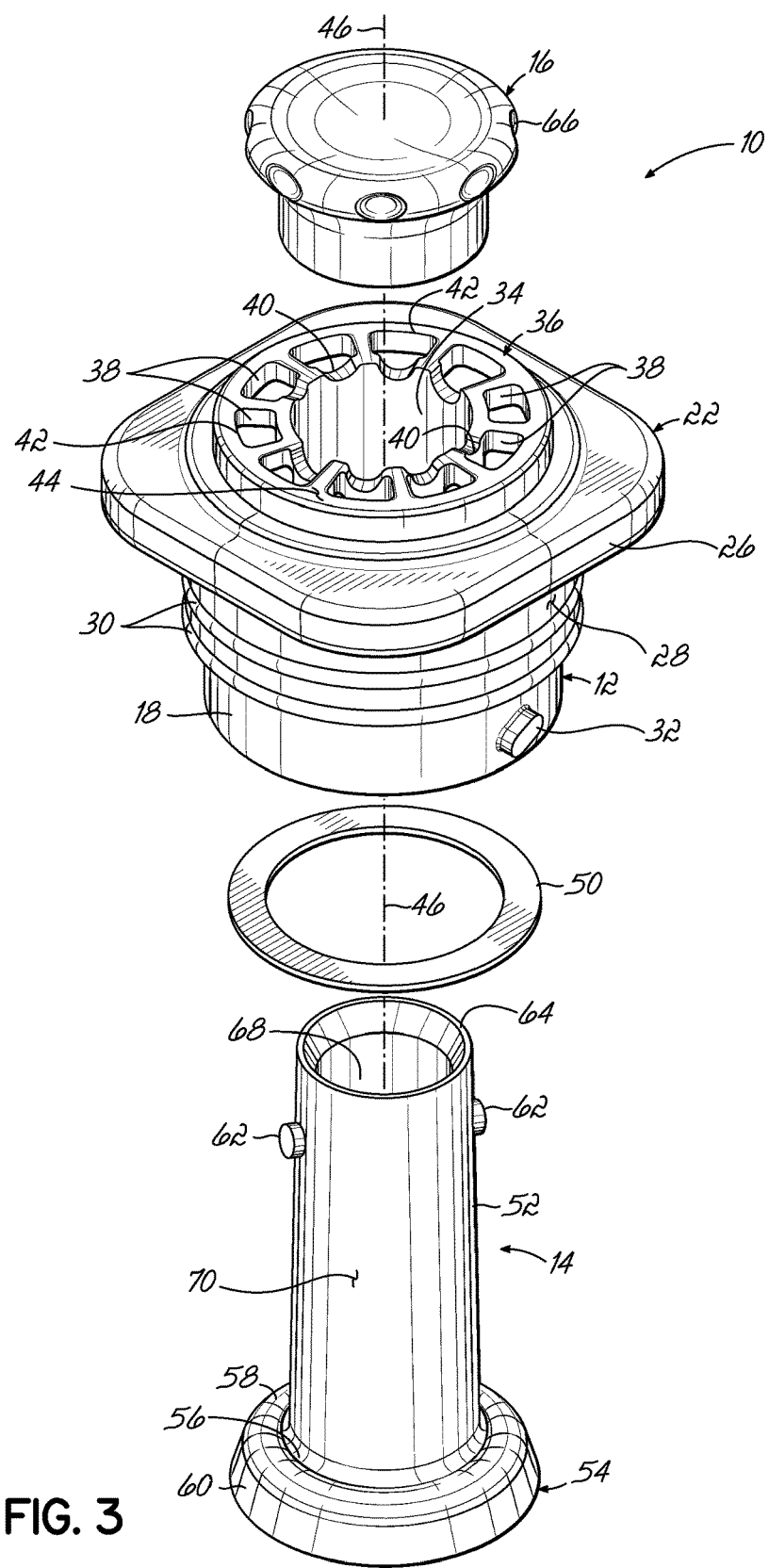
FIG. 3 is an exploded, perspective view of the closure shown in FIG. 1.

Referring now to the figures and, in particular, to FIGS. 1-3, a closure 10 in accordance with one embodiment of the present invention is shown. The closure 10 generally includes a closure body 12, a vent valve 14, and a port cap 16.

Figure 4:
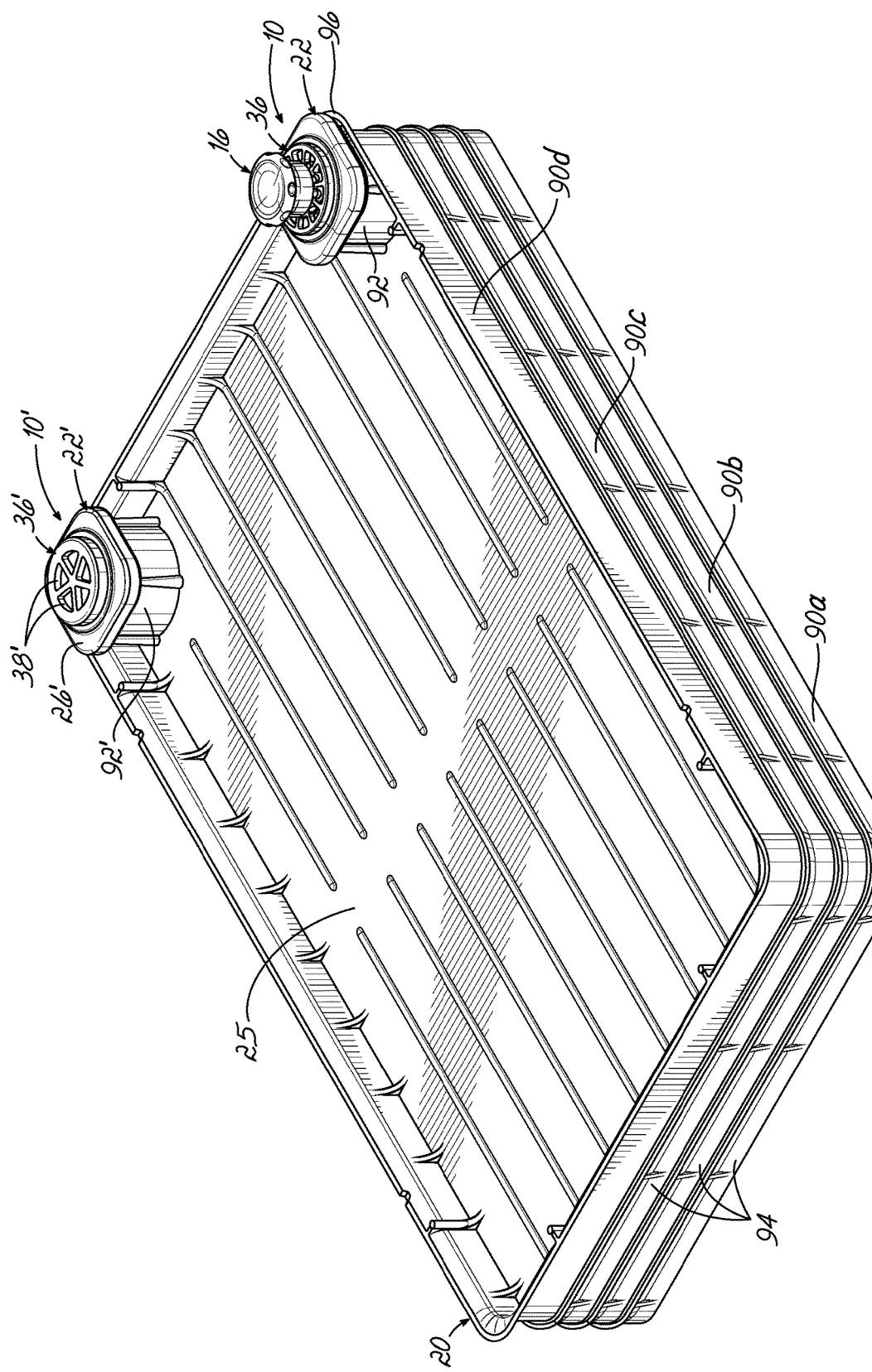
FIG. 4 is a perspective view of a cell culture factory having two closures in accordance with two embodiments of the present invention.

The closure body 12, may be substantially cylindrical in shape, as shown, and comprise an outer sidewall 18 that may engage a gripping structure 22, and/or directly contact the opening 92 (FIG. 4) of a container 20 (FIG. 4). The gripping structure 22 may include a laterally extending portion 26 that is configured or is shaped and/or textured to accommodate a user's grip on the closure 10 during insertion or removal of the closure 10 with respect to the container 20 that defines an enclosed chamber or space 25. Optionally, the gripping structure 22 may be constructed from, or be coated with, an elastomeric material to further facilitate the user's ease and comfort of use. Still further, the gripping structure 22 may include an outer surface 28 having, without limitation, indentations (not shown), at least one thread (not shown), ridges (not shown), ribs 30, etc. to facilitate a sealed, threaded, friction, or other fit engagement with the container 20.

Alternatively, or additionally, the outer sidewall 18 of the closure body 12 may include, without limitation, indentations (not shown), at least one thread (not shown), ridges (not shown), ribs (not shown), or tabs 32 that further facilitate the closure 10 engagement with the container 20.

It would be readily appreciated that while the closure body 12 and the gripping structure 22 are shown as separate molded elements that are assembled after molding, the closure body 12 may, in some embodiments, be molded to specifically include the features of the gripping structure 22, e.g., the ribs 30 and the laterally extending portion 26. In those embodiments wherein the closure body 12 and the gripping structure 22 are separately molded, the outer sidewall 18 of the closure body 12 may be keyed and/or include a surface structure ("keyed structures" 24 in FIG. 5) that match and receive the gripping structure 22.

The closure 10 may be used in any suitable labware container, for example, any type of cell culture vessel including, without limitation, stacked trays 90. Exemplary stacked trays 90 may include, for example, the commercially-available NUNCLON Δ Surface Cell Factory System (Nunc A/S, Roskilde, Denmark) or the stacked cell factory described in U.S. application Ser. No. 14/366,098, entitled CELL CULTURE DEVICE, filed on even date herewith, the disclosure of which is incorporated herein by reference in its entirety. While the various embodiments of the present invention are specifically shown as being directed to cell culture applications, for example, culture trays, it would be appreciated that the closure 10 may also be used with other containers, including, for example, roller bottles and/or flasks.

Briefly, the container 20, as shown, is a cell culture device having a stack of culture trays 90a, 90b, 90c, 90d, wherein gas exchange between the chamber or space 25 and an exterior of the container 20 occurs via one or more venting port openings 92 in fluid communication with the interior chamber or space 25. Each tray 90a, 90b, 90c, 90d comprises at least one growth surface, wherein a bottommost tray 90a may also form a floor or bottom of the container 20. At least one side wall 94 extends upwardly from the bottom of the bottommost tray 90a, and a top tray 90d in the stack may serve as the top cover or, alternatively, a separate cover piece (not shown) may be used. For this particular embodiment, the top tray 90d includes the one or more venting port openings 92, 92' each receiving a closure 10, 10' in accordance with one or more embodiments of the present invention. In some embodiments, the port openings 92 may further include a pouring spout 96.

Turning again to the details of the closure body 12, it may further include an inner sidewall 34 that, with the outer sidewall 18, extends upwardly and is operably joined with the outer sidewall 18 at a venting region or surface 36 ("venting surface" 36). The venting surface 36 may be substantially horizontal, i.e., generally orthogonal to the inner and outer sidewalls 34, 18. The venting surface 36, as shown in the illustrative embodiment, may include a plurality of openings 38 configured to permit air exchange between the exterior and the interior of the container 20 when the closure 10 is positioned within the opening of the container 20, as described in detail below.

Figure 9A:
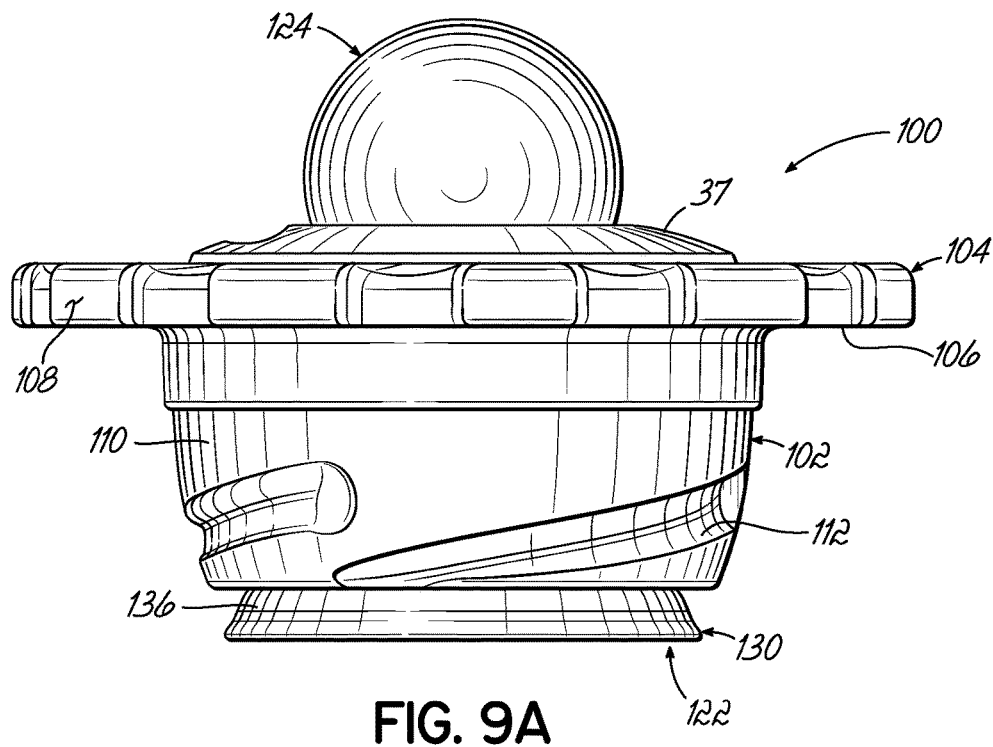
FIG. 9A is a perspective view of a closure in accordance with another embodiment of the present invention.
Figure 9B:
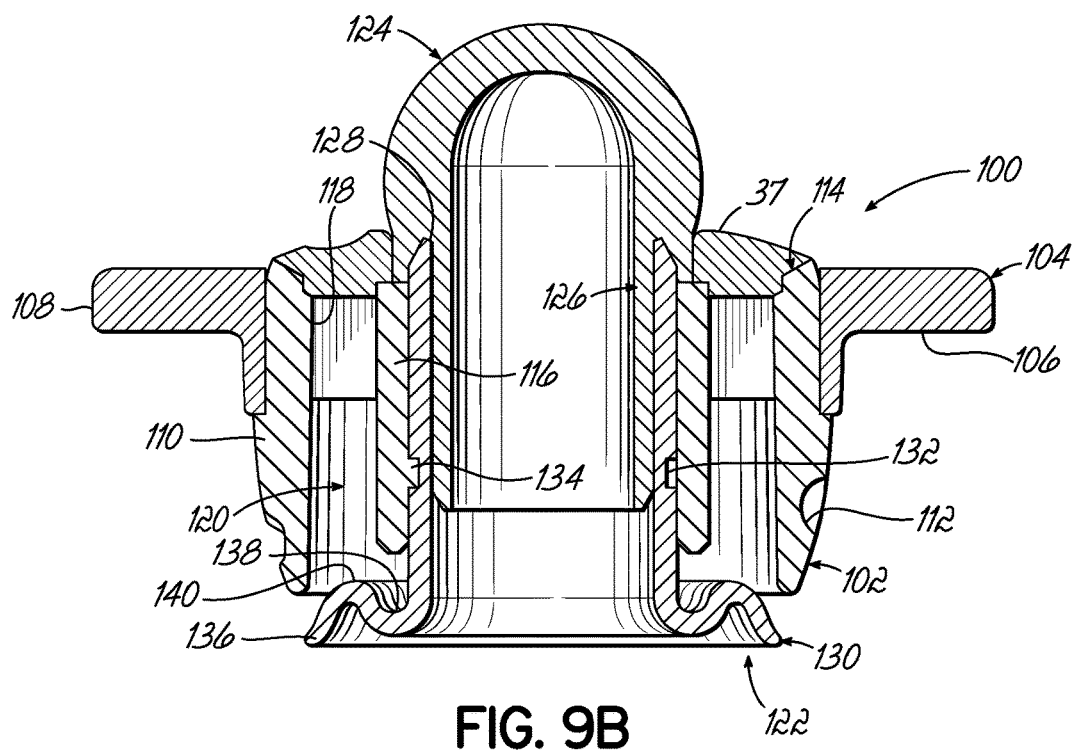
FIG. 9B is a cross-sectional view of the closure of FIG. 9A.

Though not shown, to maintain sterility of the closure 10, the venting surface 36 may include a vent cover 37 (FIG. 9). The vent cover 37 may comprise, for example, a removable, frangible tear strip, or a non-removable rotating cover which, in a first position covers the vent openings 38 to block gas exchange or, in a second position, exposes the vent openings 38 to permit gas exchange.

Referring specifically now to FIG. 3, each of the plurality of openings 38 is shown in greater detail and includes an inner and outer sidewall edge 40, 42 adjacent to the inner and outer sidewalls 34, 18, respectively. The inner sidewall edge 40 may be scallop-shaped as it extends downwardly from an upper surface 44. The scallop-shaped edge may vary in a depth dimension, such as by having a smaller or greater radius of curvature, for example, extending vertically between the upper surface 44 and the scallop-shaped edge. More specifically, each of the plurality of openings 38 has a scalloped inner sidewall edge 40 having a depth dimension, which may vary from the depth dimension of the scallop-shaped edge of an adjacent opening 38. Additionally, though not necessarily, the depth dimension of one of the plurality of openings 38 may be substantially similar to a depth dimension of a diametrically opposing one of the openings 38. Said another way, the scallop-shaped edges of the openings may be variable in depth and with or without a symmetry relative to a lengthwise central axis 46 of the closure 10.

As described with specific reference to FIGS. 1-3, the symmetric scalloped edges 40 of the openings 38 cooperate with the vent valve 14 for transitioning the closure 10 from a seal state to at least one vent state, wherein the closure 10 in one of the vent state permits air exchange between the exterior and the interior of the container 20. One method of transitioning the closure 10 between the seal state and at least one of the vent states is described in greater detail below.

Referring still to FIG. 3, a filter 50, which may be positioned and held within the closure body 12 to reduce or eliminate the passage of microorganisms through the closure 10 from the exterior of the container 20 to the interior of the container 20. The filter 50 may include a gas permeable membrane or filter made from any suitable material that permits the exchange of at least gas, such as oxygen and carbon dioxide. Suitable materials may include, without limitation, polyethylene, polytetrafluoroethylane, nitrocellulose, poly sulfones, or polyvinyldifluoride. If porous, then the pores of the filter 50 are preferably sized to block the passage of bacteria and/or fungi.

With reference again to FIGS. 1-3, the details of the illustrative embodiment of the vent valve 14 and the port cap 16 are described. The vent valve 14 may be molded using a thermoplastic material including, without limitation, polyethylene, polypropylene, polyvinyl chloride, acrylonitnle-butadiene styrene, or polystyrene and comprises a hollow, upright portion 52 (which may be substantially cylindrical). The vent valve 14 further comprises a flattened base 54 extending radially away for the upright portion 52. The flattened base 54 further includes an annular recess 56 surrounded by an annular ridge 58 having an outer wall 60 that slopes radially downward and outward. In this way, when the vent valve 14 is coaxially positioned within the closure body 12, the outer sidewall 18 of the closure body 12 may be proximate to, and/or engage the outer wall 60 to form a first seal. In some embodiments, the inner sidewall 34 of the closure body 12 may engage the annular recess 56, forming a second seal. However, in other embodiments, the inner sidewall 34 may comprise one or more ribs, which engage the annular recess 56. In still other embodiments, the inner sidewall 34 need not engage the annular recess 56.

The vent valve 14 further includes at least one boss (two diametrically opposing bosses 62 are shown) positioned proximate to a top edge 64 of the upright portion 52. Each of the bosses 62 may have an outer surface shape that substantially matches, and is thereby received by, the radii of curvature of the scalloped edges 40. The positioning of the bosses 62 relative to the scalloped edges 40 (with respect to the depth dimension) determines the venting or sealing state of the closure 10 as described in detail below.

The bosses 62 may be sufficiently spaced away from the top edge 64 of the vent valve 14 so that the top edge 64 may receive the port cap 16. The port cap 16 may be formed in any number of shapes including, without limitation, rounded or domed as shown in FIG. 9 or flattened with a gripping ridge 66 as shown in FIG. 3. The port cap 16 closes a lumen, bore, or port 68 extending through the vent valve 14. The port cap 16 may be removable from the vent valve 14 so as to provide fluidic communication between the exterior and the interior of the container 20 and as described in detail below. Otherwise, the port cap 16 may be permanently secured to the vent valve 14 if fluid communication is neither desired nor necessary.

Figure 5:
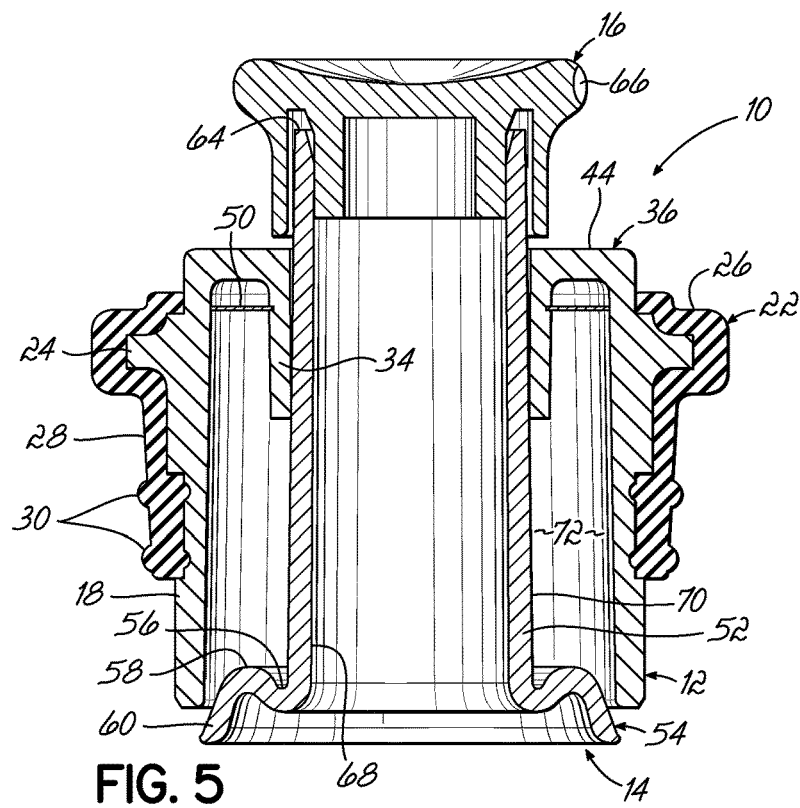
FIG. 5 is a cross-sectional view of the closure taken along the line 5-5 in FIG. 1.
Figure 6:
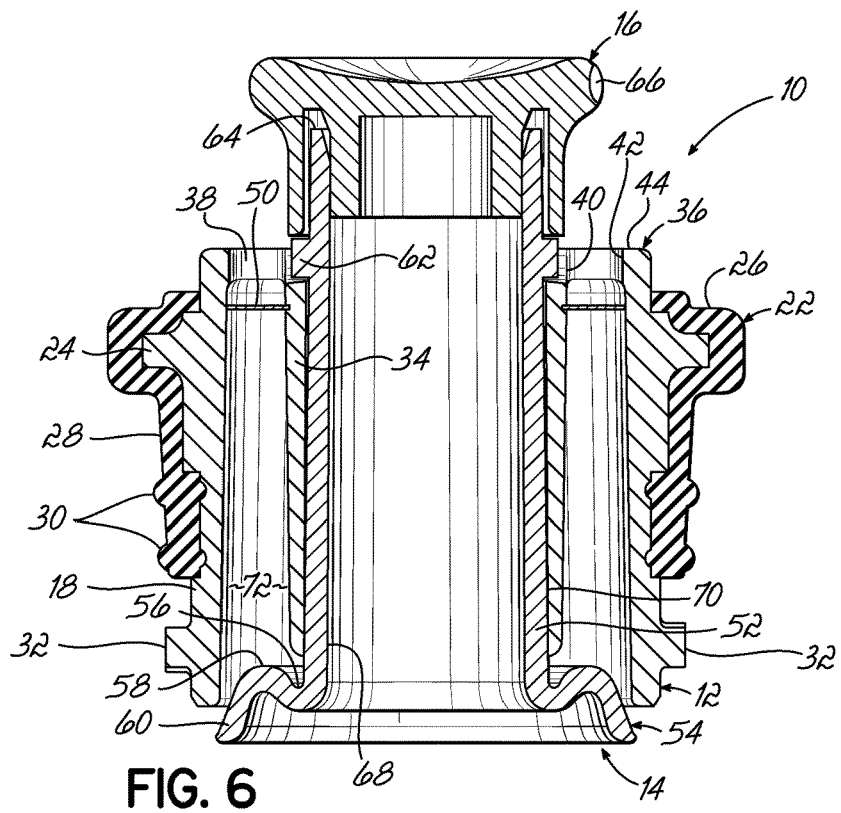
FIG. 6 is a cross-sectional view of the closure taken along the line 6-6 in FIG. 1.

With reference now to FIGS. 3, 5, and 6, assembly of the closure 10 is described in greater detail. The vent valve 14 may be positioned within the closure body 12 such that an outer surface 70 of the vent valve 14 is positioned proximate the inner sidewall 34 of the closure body 12. Accordingly, the annular ridge 58 may reside, at least partially, within a communicating volume 72 provided between the inner and outer sidewalls 34, 18 of the closure body 12. The filter 50 is positioned within communicating volume 72 of the closure body 12, generally proximate the plurality of openings 38; however, the position of the filter 50 is not limited to the specific illustrative embodiment.

Figure 7A:
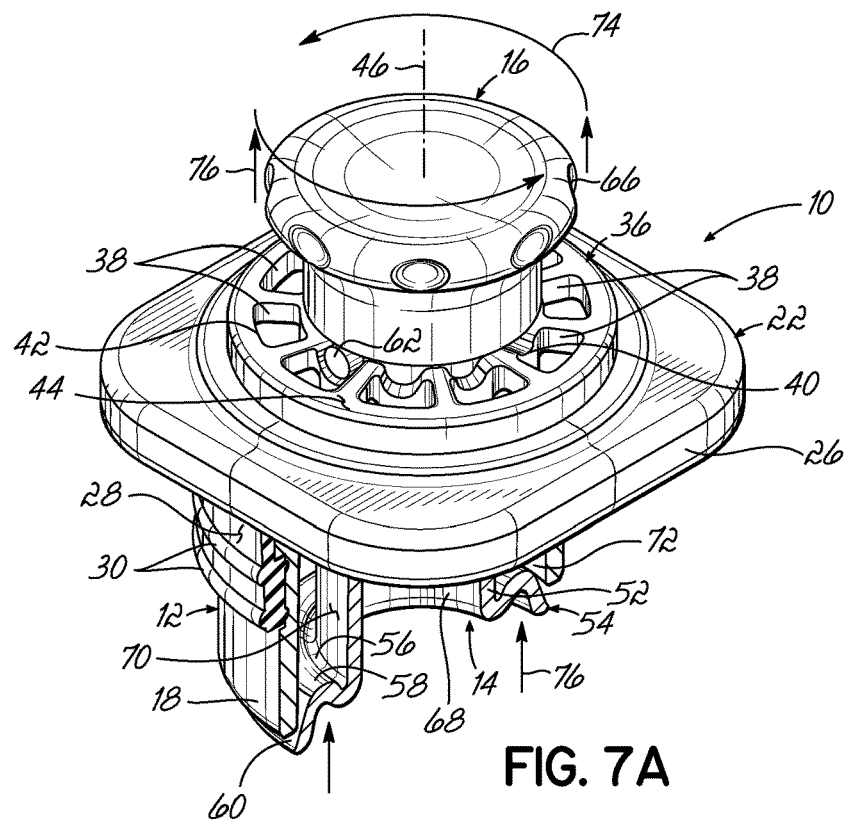
FIG. 7A is a perspective view of the closure, with the sealing portion shown in cross-section and in the vent state.
Figure 7B:
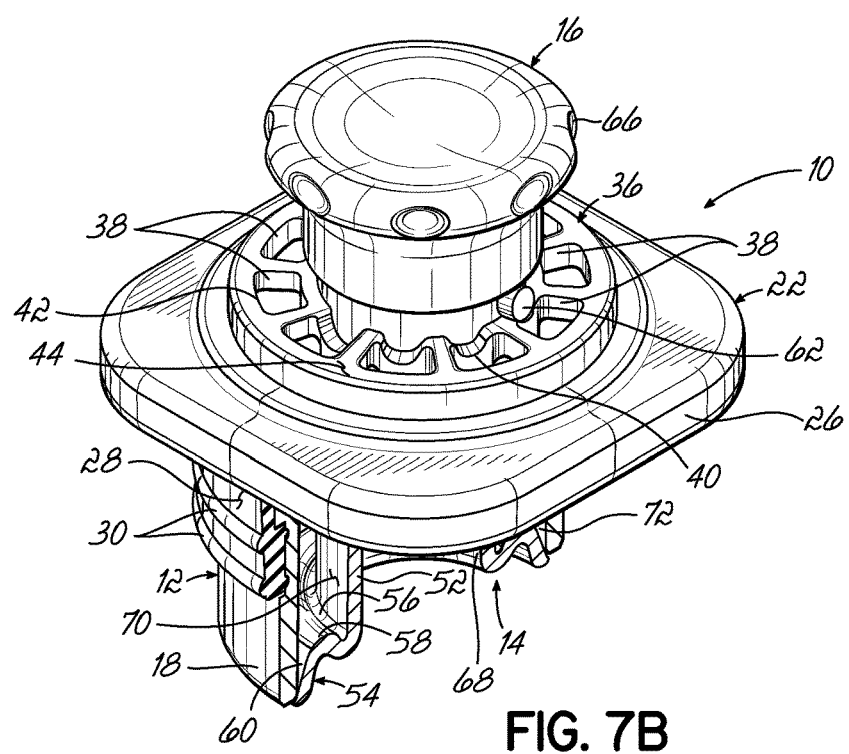
FIG. 7B is a perspective view of the closure, with the sealing portion shown in cross-section and in the seal state.

Accordingly, and with reference now to FIGS. 7A and 7B, with the vent valve 14 positioned within the closure body 12, the bosses 62 may reside along the venting surface 36 or, more specifically, within one of the scalloped edges 40 of the openings 38. More specifically, and as is shown, ten openings 38 are provided within the venting surface 36, or rather, two sets of five openings 38. One of the openings 38 of each set has a maximum depth dimension such that the boss 62 is nearly completely received by and resides within the scalloped inner wall edge 40. With the bosses 62 in this position (i.e., a full vent state), the vent valve 14 is fully extended downwardly within and with respect to the closure body 12 and the outer wall 60 of the flattened base 54 is spaced away from the outer sidewall 18 of the closure body 12. Accordingly, one or more gases may be exchanged through the closure 10 by entering the closure body 12 through the plurality of openings 38, passing through the filter 50, moving through the communicating volume 72, and out of the closure body 12 from between the outer sidewall 18 and the outer wall 60 of the flattened base 54. Gas may also move in the opposing direction as well.

The vent valve 14 with the port cap 16 may be rotated about the lengthwise central axis 46 and with respect to the closure body 12 such that the bosses 64 of the vent valve 14 move, successively, into the scalloped inner wall edge 40 of the adjacent one of the plurality of opening 38. Again, in the particular illustrative embodiment, rotation of the vent valve 14 in the counterclockwise direction (indicated by the arrows 74) causes the bosses 64 to reside in a scalloped edge 40 having a successively smaller depth dimension. With each decrease in the depth dimension, the vent valve 14 is directed upwardly with respect to the closure body 12 and the outer wall 60 of the flattened base 54 of the vent valve 14 is brought into closer proximity to the outer sidewall 18 of the closure body 12 (as indicated by the arrows 76) (i.e., a partial vent state). As a result, the volume of gas exchange may be reduced. Said another way, the closure 10 may be not only selectively vented but also variably vented and thus need not be limited to the full vent state and a seal state, the latter of which is described in greater detail below.

With further rotation of the vent valve 14 with respect to the closure body 12, the bosses 62 move to those openings 38 having an inner wall edge 40 having the smallest depth dimension or, as shown, is substantially coplanar with the outer wall edge 42. In this position (i.e., the seal state) the vent valve 14 is fully directed in the upward position with respect to the closure body 12. In this position, the outer wall 60 of the flattened base 54 of the vent valve 14 resides adjacent to and forms a seal with the outer sidewall 18 of the closure body 12. As a result, gas exchange may be optionally terminated, if and when desired or necessary (such as when moving the container 20 (FIG. 4) from a controlled environment).

Figure 8C:
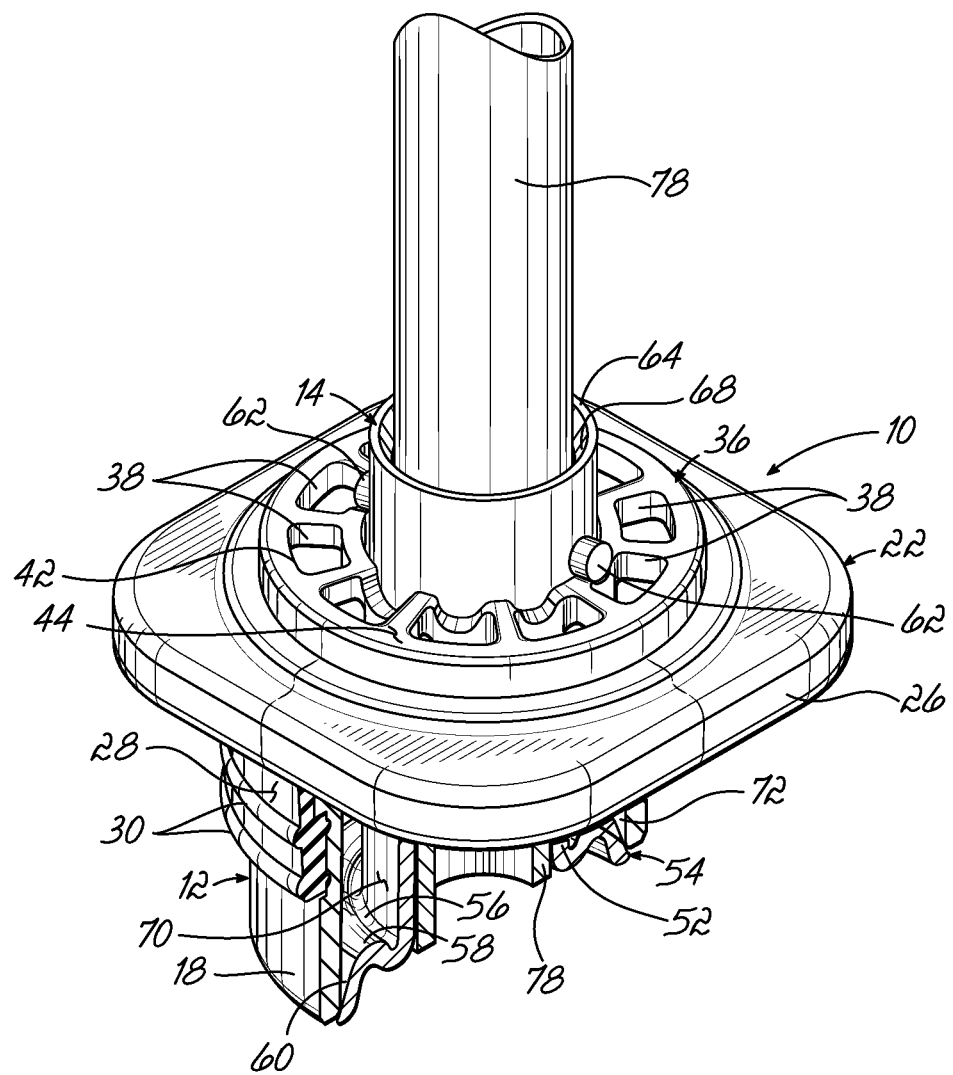
FIG. 8C is a perspective view of the closure, with the sealing portion shown in cross-section and in the seal state, and with the tubing extending through the port.

With reference now to FIG. 8A-8C a method of using the closure 10 in accordance with another embodiment of the invention is shown. As shown in FIG. 8A, the port cap 16 (FIG. 1) is removed from the vent valve 14, which opens the port and permits fluidic communication between the exterior and the interior of the container 20 (FIG. 4). In this way, a tube 78, adapter 170 (FIG. 15C), and the like, may be inserted into the vent valve 14 for fluid exchange, such as the removal or addition of culture medium, additives, and/or cells. More specifically, a sterile tubing 78 that is fluidically coupled to a sterile culture medium supply (not shown) may be directed into the port 68 of the vent valve 14, as shown in FIG. 8B (indicated by arrow 80).

With the tube 78 fully inserted, the tube 78 with the vent valve 14 may be operated in a manner that is similar to the description provided above with respect to the vent valve 14 and the port cap 16. That is, the tube 78 with the vent valve 14 may be rotated (indicated by arrow 82) to bring the outer wall 60 of the flattened base 54 of the vent valve 14 into vent and/or seal states with the outer sidewall 18 of the closure body 12 (indicated by arrow 84). Additionally, the closure 10 may be vented (in the full or partial vent state) while growth medium or additives are directed into the container 20 by further rotation of the vent valve 14 with the tube 78. Though not specifically shown, the tube 78 may be withdrawn from the vent valve 14 and the port cap 16 replaced.

Accordingly the closure 10 of FIGS. 1-8C is configured to reversibly provide one or more vent states and a seal state for gas exchange, and an open port for fluid communication.

Figure 10:
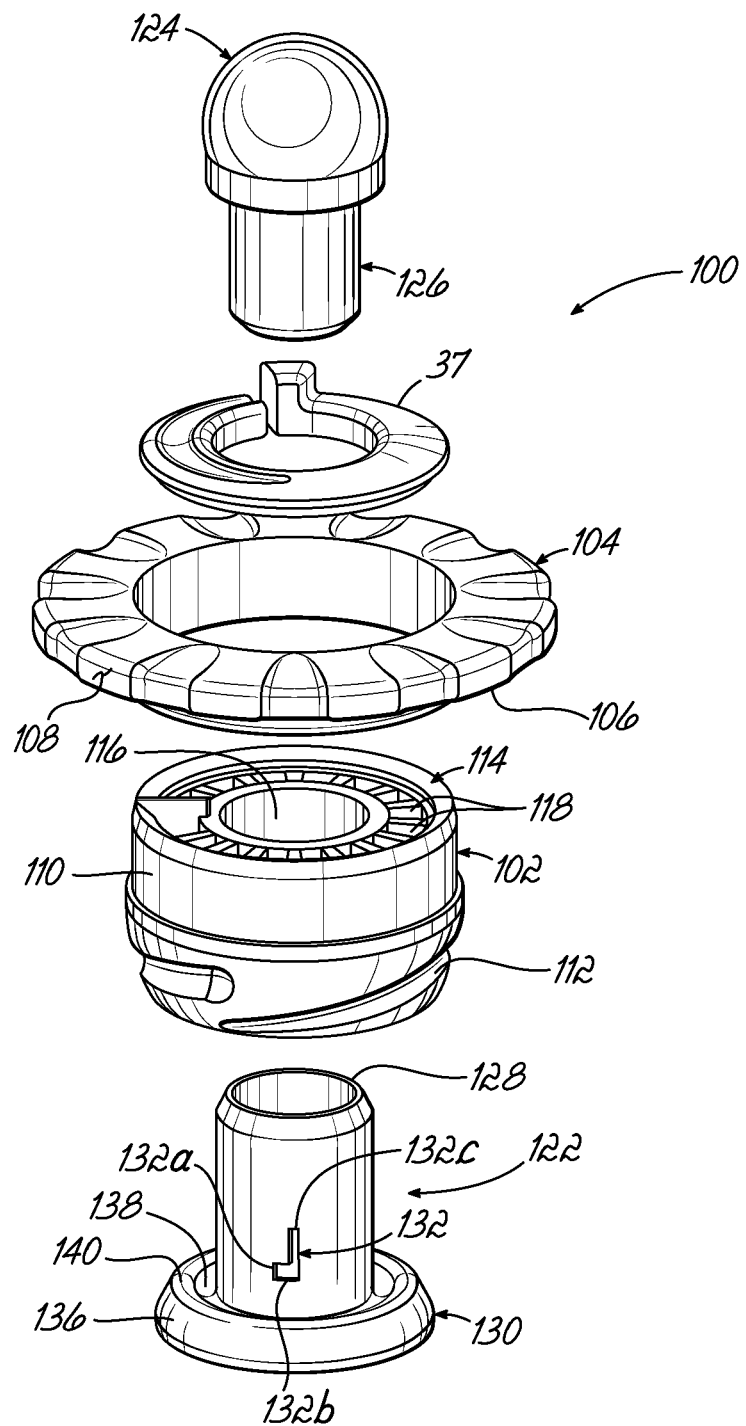
FIG. 10 is an exploded, perspective view of the closure of FIG. 9A.

With reference now to FIGS. 9 and 10, a closure 100 in accordance with another embodiment of the present invention is shown and described. The closure includes a closure body 102 with a gripping structure 104 secured thereto. The gripping structure 104, as was describe previously, may include a laterally extending portion 106 and a textured outer surface 108 for facilitating the manipulation of the closure 100. Again, though not shown, the gripping structure 104 may be molded as a unitary structure with the closure body 102.

The closure body 102 may again include an outer sidewall 110 having at least one outer thread 112 configured to form a fluid tight seal with the opening 92 (FIG. 4) of the container 20 (FIG. 4). As noted previously, the outer thread 112 may be replaced with a rib 30 (FIG. 1) or other structure for forming the fluid tight seal. The closure body 104 further includes a venting region or surface 114 ("venting surface" 114) and an inner sidewall 116, wherein the venting surface 114 includes the vent cover 37 configured to maintain sterility of the closure 100 until the venting surface 114 is ready for its intended use.

The venting surface 114 may include a plurality of openings 118, as was described previously, wherein the openings 118 are configured to provide gas exchange between the exterior and the interior of the container 20 (FIG. 4) via the communicating volume 120. The venting surface 114 may include a filter 50 (FIG. 3) or other structures for decreasing or eliminating the passage of microorganisms. One example of a filter may include pores ranging in size from about 0.2 µm to about 0.45 µm, to block the passage of at least most microorganisms, particularly airborne bacteria and fungi.

The vent valve 122 of the closure 100 shown in FIGS. 9 and 10 may be shaped in a manner that is similar to the vent valve 14 of FIG. 1. However, in the instant embodiment, the vent valve 122 is operably coupled to the port cap 124 via a plug 126. In that regard, the port cap 124 is coupled to a top edge 128 of the vent valve 122, which generally opposes the flattened base 130 of the vent valve 122. Thus, the plug 126 and the port cap 124 are removed from the closure 100 prior to inserting a tube 78 (FIG. 7A) or the adaptor 170 (FIG. 15C), as was described previously.

Returning again to the vent valve 122, it may include one or more recessed surfaces 132 configured to receive one or more tabs or lugs 134 formed on the inner sidewall 116 of the closure body 102. In some embodiments, the recessed surface 132 may include at least one thread so that the vent valve 122 threadably engages, and moves relative to, the lug 134 and the closure body 102. In other embodiments, such as the illustrative embodiment, the recessed surface 132 may be substantially "L"-shaped. In that regard, the recessed surface 132 may include a substantially horizontal portion having first and second ends 132a, 132b and a vertical portion extending from the second end 132b to a third end 132c. Thus, when the lug 134 resides in the first end 132a of the horizontal portion, the vertical position of the vent valve 122 with respect to the closure body 102 is substantially secured. The vent valve 122 may then be rotated such that the lug 134 resides in the second end 132b of the horizontal portion and then directed upwardly such that the lug 134 resides within the third end 132c. Upward movement of the vent valve 122 causes the outer wall 136 of the flattened base 130 to engage and form a seal with the outer sidewall 110 of the closure body 102. Further, the inner sidewall 116 may reside in the annular recess 138 and between the vent valve 122 and the annular ridge 140 on the flattened base 130 for the seal state, as was described above. Movement of the vent valve 122 in the reverse direction transitions the closure 100 into a vent state.

FIGS. 11A-C and 12A-C illustrate still another embodiment of a closure 150 that is similar to the device 100 of FIG. 9A, wherein like reference numerals refer to like parts, and a method of using the same as an open port to the container 20 (FIG. 4). The closure 150 includes a tabbed port cap 152 that is configured to be rotated and removed from the closure 150. In FIGS. 11A and 12A, the vent valve 122 is in the vent state and the tabbed port cap 152 is secured in a lower position; however, the vent cover 37 remains on the venting surface 114 and thus gas exchange does not occur between the exterior and the interior of the container 20 (FIG. 4). In FIGS. 11B and 12B, the tabbed port cap 152 has been rotated and pulled upwardly to direct the flattened base 130 of the vent valve 122 toward the outer sidewall 110 of the closure body 102 and placing the closure 150 in the seal state. In FIGS. 11C and 12C, the port is opened by removing the port cap 152 while the vent valve 112 is in the seal state.

Figure 13A:
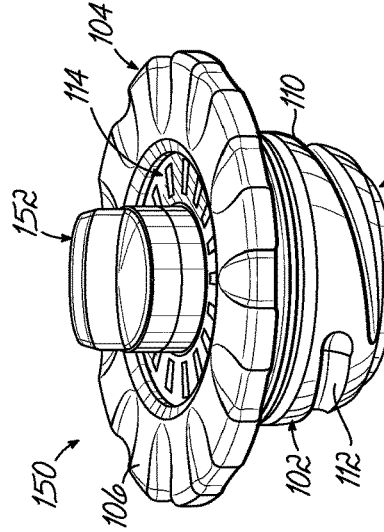
FIGS. 13A-13C are a series of perspective views of a closure and a method of using the same in accordance with another embodiment of the present invention.
Figure 13B:
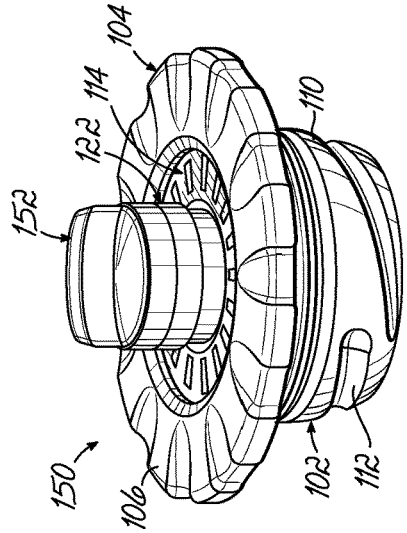
Figure 13C:
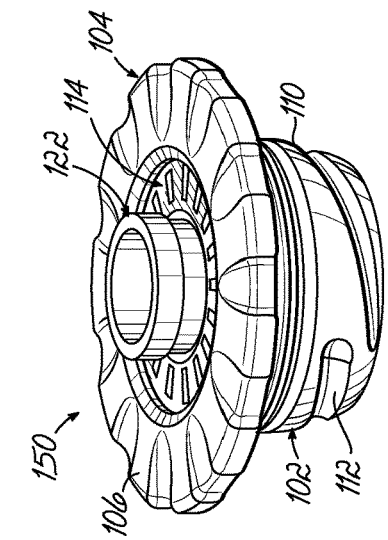
Figure 14A:
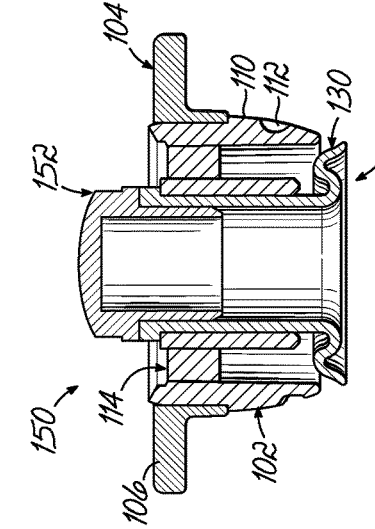
FIGS. 14A-14C are cross-sectional views of the closure of FIGS. 13A-13C, respectively.
Figure 14B:
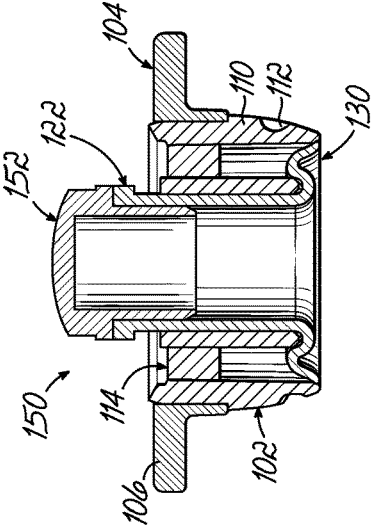
Figure 14C:
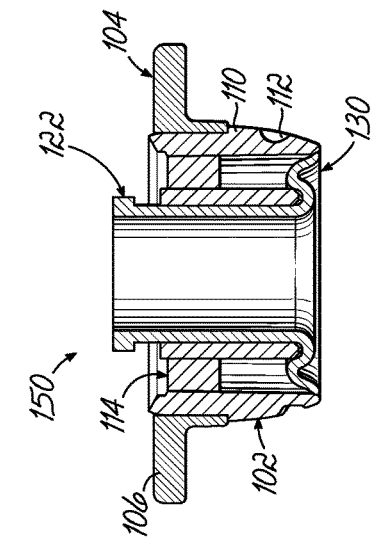

FIGS. 13A-13C and 14A-14C are similar to FIGS. 11A-C and 12A-C but illustrate a method of both venting and opening the port. Accordingly, in FIGS. 13A and 13C, the venting surface 114 of the closure 150 is opened by removing the vent cover 37 (FIG. 11A) while the vent valve 122 is in the vent state and the tabbed port cap 152 is secured in a lower position. In FIGS. 13B and 14B, the tabbed port cap 152 is rotated and pulled upwardly to direct the flattened base 130 of the vent valve 122 toward the outer sidewall 110 of the closure body 102 and place the closure 150 in the seal state. In FIGS. 13C and 14C, the port is opened by removing the port cap 152 while the venting surface 114 via the vent valve 112 in the seal state.

Figure 15A:
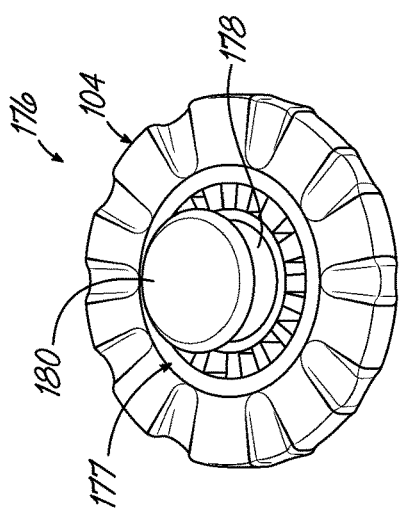
FIGS. 15A-15B and 15D-15F are perspective views of closure surfaces in accordance with various embodiments of the present invention.

FIGS. 15A-15F illustrate various closure surfaces in accordance with additional embodiments of the present invention. In FIG. 15A, a closure surface 160 in accordance with one embodiment of the present invention includes a venting surface 162 with openings formed concentrically around a sealed port 164. Accordingly, a fluid port is available only if the closure surface 160 is removed.

Figure 15B:
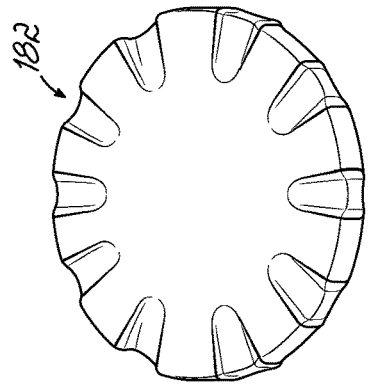

FIG. 15B illustrates a closure surface 166 according to another embodiment of the present invention that lacks a venting surface (i.e., no openings) but that includes a port 168 extending upwardly therefrom. Accordingly, while the port may be open in the closure surface 166, venting is not possible.

Figure 15C:
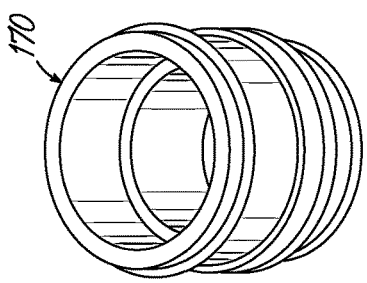
FIG. 15C is a perspective view of an adaptor for use with a closure in accordance with one embodiment of the present invention.

FIG. 15C illustrates one example of an adaptor 170 for use with a closure surface having an open port and in accordance with the one embodiment of the present invention. The adaptor 170 may be inserted into the opened port and is configured to receive a tube 78 (FIG. 7A) for adding or removing fluid as described previously.

Figure 15D:
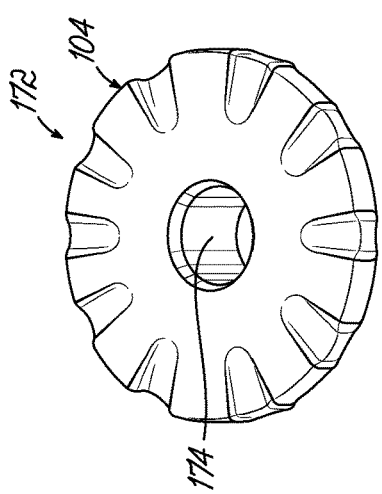

FIG. 15D illustrates a closure surface 172 in accordance with one embodiment of the present invention and that is similar to the closure surface 166 of FIG. 15B. However, in FIG. 15D, instead of extending upwardly from the closure surface 166, the port 174 is flush with the closure surface 172.

Figure 15E:
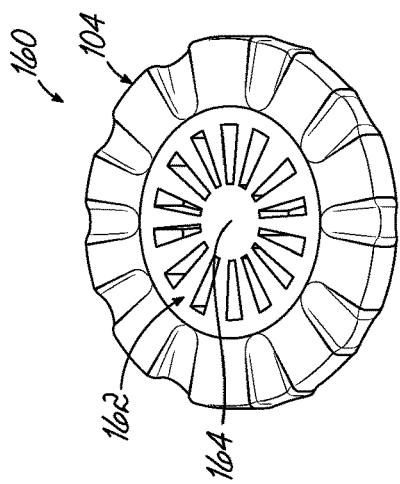

FIG. 15E illustrates a closure surface 176 according to yet another embodiment of the present invention having a venting surface 177 with a plurality of openings and including a port 178 extending upwardly therefrom. Rather than including a port cap 16, 124 (FIGS. 1 and 8), the port 178 may be closed with a lid 180, which may be removable or permanently secured to the port 178.

Figure 15F:
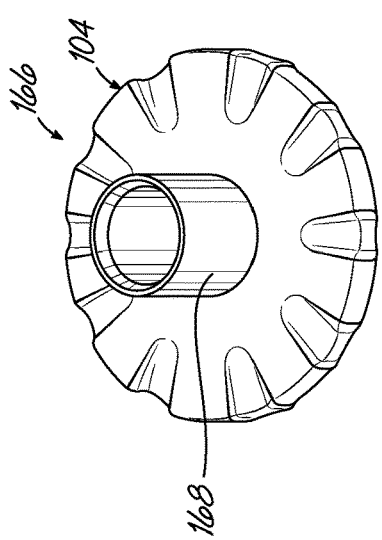

FIG. 15F illustrates a closure surface 182 in accordance with one embodiment of the present invention comprising a solid surface that connects the outer sidewall 18 (FIG. 5A) with the inner sidewall 34 (FIG. 5A). Instead, venting is allowed via removal of the closure surface 182.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A closure for a labware device defining an interior chamber and having at least one opening in fluid communication with the interior chamber, the closure comprising:
   a closure body configured to be mounted to the labware device and in fluid communication with the at least one opening, the closure body having a venting region, an outer sidewall and an inner sidewall operably coupled to the outer sidewall by the venting region;
   a vent valve mounted within the closure body for upward and downward movement relative to the closure body and defining a space between the closure body and the vent valve, the space defining a path between the closure body and the vent valve for gas exchange between the interior chamber and the exterior of the labware device through the venting region of the closure body, wherein the venting region comprises a plurality of openings in communication with the space and the vent valve includes at least one boss thereon, and the venting region having a shape defining a plurality of positions, each of the plurality of positions being shaped to engage the least one boss of the vent valve; and
   a filter positioned within the space and configured to filter contaminants from a gas entering the interior chamber via the path.

2. The closure of claim 1, wherein the vent valve further comprises:
   a port extending through the vent valve; and
   a plug operably coupled to the vent valve and configured to be selectively removed from the vent valve for providing fluid communication with the interior chamber through the port.

3. The closure of claim 1, further comprising:
   a gripping structure operably coupled to the closure body and configured to mount the closure body to the labware device.

4. The closure of claim 3, wherein the gripping structure and the closure body are constructed as a unitary structure.

5. The closure of claim 1, wherein a first one of the plurality of positions has a first depth dimension and a second, adjacent one of the plurality of positions has a second depth dimension, the second depth dimension being different than the first depth dimension.

6. The closure of claim 1, wherein the closure body further comprises:
   a first end configured to be positioned proximate an exterior side of the labware device; and
   a second end configured to be positioned proximate an interior side of the labware device, the venting region being positioned proximate the first end of the closure body.

7. A closure for a labware device defining an interior chamber and having at least one opening in fluid communication with the interior chamber, the closure comprising:
   a closure body configured to be mounted to the labware device and in fluid communication with the at least one opening, the closure body having a venting region, an outer sidewall and an inner sidewall operably coupled to the outer sidewall by the venting region;
   a vent valve mounted within the closure body for upward and downward movement relative to the closure body and defining a space between the closure body and the vent valve, the space defining a path between the closure body and the vent valve for gas exchange between the interior chamber and the exterior of the labware device through the venting region of the closure body, wherein the vent valve includes at least one recess on an external surface thereof, and the inner sidewall of the closure body further includes at least one inwardly directed tab configured to be received by and move within the at least one recess; and a filter positioned within the space and configured to filter contaminants from a gas entering the interior chamber via the path.

\* \* \* \* \*